United States Patent
Ma et al.

(10) Patent No.: US 11,130,967 B2
(45) Date of Patent: Sep. 28, 2021

(54) FERTILITY RESTORATION GENE IN WHEAT AND USES THEREOF

(71) Applicants: FRONTIER LABORATORIES OF SYSTEMS CROP DESIGN CO., LTD., Beijing (CN); PEKING UNIVERSITY, Beijing (CN)

(72) Inventors: Ligeng Ma, Beijing (CN); Zheng Wang, Beijing (CN); Jian Li, Beijing (CN); Hang He, Beijing (CN); Shaoxia Chen, Beijing (CN); Xingwang Deng, Beijing (CN)

(73) Assignees: BEIJING NEXT GENERATION HYBRID WHEAT BIOTECHNOLOGY CO., LTD, Beijing (CN); PEKING UNIVERSITY INSTITUTE OF ADVANCED AGRICULTURAL SCIENCES, Weifang (CN)

(*) Notice: Subject to any disclaimer, the term of this patent is extended or adjusted under 35 U.S.C. 154(b) by 70 days.

(21) Appl. No.: 16/320,105

(22) PCT Filed: Jul. 24, 2017

(86) PCT No.: PCT/CN2017/094012
§ 371 (c)(1),
(2) Date: Jan. 24, 2019

(87) PCT Pub. No.: WO2018/019193
PCT Pub. Date: Feb. 1, 2018

(65) Prior Publication Data
US 2019/0338305 A1 Nov. 7, 2019

(30) Foreign Application Priority Data

Jul. 25, 2016 (CN) .......................... 201610588768.4
Jul. 21, 2017 (CN) .......................... 201710599589.5

(51) Int. Cl.
*C12N 15/82* (2006.01)
*C07K 14/415* (2006.01)
*C12N 15/52* (2006.01)

(52) U.S. Cl.
CPC ........ *C12N 15/8287* (2013.01); *C07K 14/415* (2013.01); *C12N 15/52* (2013.01); *C12N 15/8209* (2013.01); *C12N 2830/007* (2013.01); *C12N 2830/008* (2013.01); *C12N 2830/65* (2013.01)

(58) Field of Classification Search
None
See application file for complete search history.

(56) References Cited

FOREIGN PATENT DOCUMENTS

| CN | 1570103 A | 1/2005 |
|---|---|---|
| CN | 101243770 A | 8/2008 |
| WO | 02059269 A2 | 8/2002 |
| WO | 2013064085 A1 | 5/2013 |
| WO | 2016048891 A1 | 3/2016 |
| WO | 2016/100309 A1 | 6/2016 |

OTHER PUBLICATIONS

Matsumoto et al (2011, NCBI Accession No. AK372683).*
Bowie et al, (1990, "Deciphering the Message in Protein Sequences: Tolerance to Amino Acid Substitutions", Science 247:1306-1310).*
McConnell et al, (2001, "Radial Patterning of Arabidopsis Shoots By Class III HD-ZIP and KANADI Genes", Nature 411 (6838)709-713).*
Kano-Murakami et al (1993, "A Rice Homeotic Gene, OSH1, Causes Unusual Phenotypes in Transgenic Tobacco", FEBS 334:365-368).*
Zhou et al (Aug. 2008, "Cultivation Method for Wheat Hybridization with Nuclear Male Sterility", Publication No. CN101243770).*
"PREDICTED: *Aegilops tauschii* subsp. tauschii vegetative cell wall protein gp1-like (LOC109749084), mRNA", GENBANK: XM_020308073.1, Feb. 24, 2017(Feb. 24, 2017), sequence CDS.
"*Hordeum vulgare* subsp. vulgare mRNA for predicted protein, complete cds, clone: NIASHv3009E08", GENBANK: AK372683.1, May 20, 2011(May 20, 2011), sequence CDS.
Bömer, A. et al., "Genetics and molecular mapping of a male fertility restoration locus (Rfg1) in rye (*Secale cereale* L.)", Theor Appl Genet, vol. 97, Dec. 31, 1998(Dec. 31, 1998), pp. 99-102.
Ahmed, T.A. et al., "QTL analysis of fertility-restoration against cytoplasmic male sterility in wheat", Genes Genet. Syst., vol. 76, Dec. 31, 2001(Dec. 31, 2001), pp. 33-38.
Kojima, T. et al., "High-Resolution RFLP Mapping of the Fertility Restoration (Rf3) Gene against Triticum Timopheevi Cytoplasm Located on Chromosome 1BS of Common Wheat", Genes Genet. Syst., vol. 72, Dec. 31, 1997 (Dec. 31, 1997), pp. 353-359.

(Continued)

*Primary Examiner* — Vinod Kumar
(74) *Attorney, Agent, or Firm* — Gang Yu

(57) ABSTRACT

A fertility restoration gene in wheat and uses thereof, belonging to the field of plant biotechnology, specifically relating to the cloning of a recessive nuclear male sterility gene and a promoter thereof, and uses thereof in hybrid breeding. The fertility restoration gene FRG1 was successfully cloned by flow cytometry and high-throughput sequencing. The FRG1 gene can completely restore the male fertility of a Lanzhou genic male sterile mutant or allelic mutants thereof, which lays a foundation for the construction of a new wheat hybrid breeding technology system, meanwhile, which provides more possibilities to solve the technical bottlenecks of "three lines" and "two lines" hybridization technology of wheat, such as unstable fertility of sterile lines, limited resources for hybrid variety, the complexity of seed production technology and the high cost of seed production. The provided gene and method for propagation and maintenance of the sterile line have important significance and application value for hybrid breeding in wheat.

15 Claims, 2 Drawing Sheets

Specification includes a Sequence Listing.

(56) References Cited

OTHER PUBLICATIONS

Liu, Dongtao et al., "Research Progresses in the Fertility Gene Mapping of the Male Sterile Gene in Wheat", Tritical Corps, vol. 19, No. 4, Jul. 31, 1997(Jul. 31, 1997), pp. 6-11.
Li, B.H. et al., "A Dominant Gene for Male Sterility in Wheat", Plant Breeding., vol. 97, Dec. 31, 1986 (Dec. 31, 1986), pp. 204-209.
Zheng, Hongyuan et al., "Identification of restorer genes of K-type CMS in wheat by cDNA-AFLP", Journal of Henan Agricultural University, vol. 48, No. 2, Apr. 30, 2014(Apr. 30, 2014), pp. 117-122.
Zhou, Kuanji et al.: "Establishment of 4E-ms Hybrid Wheat Production System", Gansu Agr. Sci. and Techn., Oct. 20, 1998 (Oct. 20, 1998), No. 10, pp. 24-26.
Schnable PS et al.:"*Zea mays* putative alpha-amylase family protein (LOC100383492), mRNA", Genebank Database, Dec. 5, 2015 (Dec. 5, 2015), Retrieved from the Internet: URL: https://www.ncbi.nlm.nih.gov/nuccore/293334594.
Wang, Shihong et al.:"Technical Difficulties and Solutions of Applying 4E-ms System in Hybrid Wheat Production", Journal of Triticeae Corps, Nov. 5, 2013 (Nov. 5, 2013), No. 6, pp. 1312-1315.
Chen, Rui-hong et al.: "Mitochondrial Proteomic Analysis of Cytoplasmic Male Sterility Line and Its Maintainer in Wheat", Agricultural Sciences in China, Jun. 30, 2010 (Jun. 30, 2010), No. 6, pp. 771-782.
Giri P. Joshi et al.: "Development of a self-fertile ditelosomic line for the long arm of chromosome 4B and its characterization using SSR markers", Genes Genet. Syst., Oct. 1, 2013 (Oct. 1, 2013), vol. 88, pp. 311-314.

\* cited by examiner ial application no. PCT/CN2017/094012 filed on 24 Jul. 2017.

SEQUENCE LISTING

<160> NUMBER OF SEQ ID NOS: 11

<210> SEQ ID NO 1
<211> LENGTH: 1878
<212> TYPE: DNA
<213> ORGANISM: Elytrigia elongata

<400> SEQUENCE: 1

```
atggagagat cccggcgcct gctgctcgtg gcgggcctgc tggcggcgct gctcccggcg      60
gcggcggccg cgttcgggcc gcagccgggg gcgccgtgcg agcccacgct gctggcgacg     120
caggtggcgc tcttctgcgc gcccgacatg cccaccgcgc agtgctgcga gcccgtcgtc     180
gccgccgtcg acctcggcgg cggcgtcccc tgcctctgcc gcgtcgccgc ggagccgcag     240
ctcgtcatgg cgggcctcaa cgccacccac ctcctcacgc tctacagctc ctgcggcggc     300
ctccgccccg gcggcgccca cctcgccgcc gcctgcgaag gtacgcaccg cacgtcgcct     360
ccttccctcc ctccctctac gtgccgattt tctgtgctcg ctttcctgct tacctagtag     420
tacgtagttt cccatggctt ctcgagtcgc tatagtgctc cgatttgggt cggtttcctc     480
```

```
gctgttctac cggatctgtc ggcacggcgc gcggcgtcgg gttctcgccg tctcccgtgg    540
cgagcgacct gcgcagcgcg cgcacggcct agctagcttc ttcataccgc tgtaccttga    600
gatatacgga gcgatttagg gtctactctg agtatttcgt catcgtagaa cgcatgtgcc    660
acgcgcgatt gtttcatcga ttctagatct gtgtttgttc ccgcgagtta agatggatct    720
agcgccgtac gcagatgcgg aggccttgcg gtctctgtag ctcgagttat cttatctact    780
gtcgttcgac tacagtattt gcctgcttcc ttttcactgg gttatcgtg cagtagtagt    840 agccatgtcc acgccttctt gttttgaggc gatcatcgtg gacatacgtt tcctgctaca    900
gatttgagga gcactttgtt tcaaactgca acgcagcttt gctttctgca gtatcttctg    960
ccttgttttg ttctgtgcag tacctcttgc ttggtcaaaa ctgaaaacgc ttgctgtttg    1020
atcggcagag caaaagcttg ccgtgctttt cgctctgcag tgcatcgcct ctgcgtcttt    1080
tcccaaacat ttccgcgttg atcctctggc ggcactgctt ttttgcatgc ggtttccgta    1140
gccttcctat ttcgtgaaaa aaggttgggt caaatcaaat ggatcgccta ttggcagagc    1200
agcagcagca acagatagct ggctgtctcg cagctttggc agaatcggtc tgtggccatc    1260
tgtcccctgc caccgttttc ctgatatttg tttctctcat ctcatcttgc ctgccactgt    1320
gcttcttttc ttgttgcgca cgtcgtcacc tctactttct ttccagattt gtttgctttt    1380
gagatacgga cgaacggctg gtaattaact ttggttgttg ttgttactgt ggatttttga    1440
cgcaggaccc gctcccccgg ccgccgtcgt cagcagcccc ccaccccgc caccgtccgc    1500 cgcacctcgc cgcaagcagc cagcgcgtac gaaccctccc tctctctctc gcctgcatct    1560
cgctctgttt atctatcttc atatgttgat cagccttgtt tacatactga catgtgctct    1620
ggatcggttt tcgcagacga cgcaccgcca ccgccgccgt cgaccgagaa gccagcgtcc    1680
ccgccgcccc aggagcacga cggcgccgcc ccccgcgcca aggccgcccc cgcccaggcg    1740
gctacctccc cgctcgcgcc cgctgccgcc accgccccgc cgccccaggc cgcgactccc    1800
gccgcggcga cggcgtcgtc caaggcggcc ttcttcttcg tcgccacggc catgctcggc    1860
ctctacatca tcctctga                                                 1878
```

`<210>` SEQ ID NO 2
`<211>` LENGTH: 663
`<212>` TYPE: DNA
`<213>` ORGANISM: Elytrigia elongata

`<400>` SEQUENCE: 2

```
atggagagat cccggcgcct gctgctcgtg gcgggcctgc tggcggcgct gctcccggcg     60
gcggcggccg cgttcgggcc gcagccgggg gcgccgtgcg agcccacgct gctggcgacg    120
caggtggcgc tcttctgcgc gcccgacatg cccaccgcgc agtgctgcga gcccgtcgtc    180
gccgccgtcg acctcggcgg cggcgtcccc tgcctctgcc gcgtcgccgc ggagccgcag    240
ctcgtcatgg cgggcctcaa cgccacccac ctcctcacgc tctacagctc ctgcggcggc    300
ctccgccccg gcggcgccca cctcgccgcc gcctgcgaag acccgctccc ccggccgcc     360 gtcgtcagca gccccccacc cccgccaccg tccgccgcac ctcgccgcaa gcagccagcg    420
cacgacgcac cgccaccgcc gccgtcgacc gagaagccag cgtccccgcc gccccaggag    480
cacgacggcg ccgccccccg cgccaaggcc gcccccgccc aggcggctac ctccccgctc    540
gcgcccgctg ccgccaccgc cccgccgccc caggcgccgc actccgccgc ggcgacggcg    600
tcgtccaagg cggccttctt cttcgtcgcc acggccatgc tcggcctcta catcatcctc    660
tga                                                                  663
```

<210> SEQ ID NO 3
<211> LENGTH: 220
<212> TYPE: PRT
<213> ORGANISM: Elytrigia elongata

<400> SEQUENCE: 3

```
Met Glu Arg Ser Arg Arg Leu Leu Leu Val Ala Gly Leu Leu Ala Ala
1               5                   10                  15

Leu Leu Pro Ala Ala Ala Ala Phe Gly Pro Gln Pro Gly Ala Pro
            20                  25                  30

Cys Glu Pro Thr Leu Leu Ala Thr Gln Val Ala Leu Phe Cys Ala Pro
            35                  40                  45

Asp Met Pro Thr Ala Gln Cys Cys Glu Pro Val Val Ala Ala Val Asp
50                  55                  60

Leu Gly Gly Gly Val Pro Cys Leu Cys Arg Val Ala Ala Glu Pro Gln
65                  70                  75                  80

Leu Val Met Ala Gly Leu Asn Ala Thr His Leu Leu Thr Leu Tyr Ser
                85                  90                  95

Ser Cys Gly Gly Leu Arg Pro Gly Gly Ala His Leu Ala Ala Ala Cys
            100                 105                 110

Glu Gly Pro Ala Pro Pro Ala Ala Val Val Ser Ser Pro Pro Pro
            115                 120                 125

Pro Pro Ser Ala Ala Pro Arg Arg Lys Gln Pro Ala His Asp Ala Pro
130                 135                 140

Pro Pro Pro Pro Ser Thr Glu Lys Pro Ala Ser Pro Pro Pro Gln Glu
145                 150                 155                 160

His Asp Gly Ala Ala Pro Arg Ala Lys Ala Ala Pro Ala Gln Ala Ala
                165                 170                 175

Thr Ser Pro Leu Ala Pro Ala Ala Thr Ala Pro Pro Gln Ala
            180                 185                 190

Pro His Ser Ala Ala Ala Thr Ala Ser Ser Lys Ala Ala Phe Phe Phe
                195                 200                 205

Val Ala Thr Ala Met Leu Gly Leu Tyr Ile Ile Leu
    210                 215                 220
```

<210> SEQ ID NO 4
<211> LENGTH: 2265
<212> TYPE: DNA
<213> ORGANISM: Elytrigia elongata

<400> SEQUENCE: 4

```
gctttgccta catactctag agaagttcaa cccatgatcc ataagcaagc tctcaattgc      60
tgttttgagt gtcaaagatg tggtgtttgc aacatataaa atacgaagaa acctctcaac     120
cacccttcct atttaggta cacatcactt gattcatgga caagtattga gaaacaacta     180
tcacctagct ctttcatcat gcgcctagta gtttctttgg acaagggtt gatgaggtat     240 gtttgtatat cttgagctat catttattg ttccttgaag cattcttgag aaccaccttg     300
ttcacttctt cagaaatctc tactagccat tgtataagct caaggaaatt acctttatgc     360
agtgaaactt ctttccatca tgtccacgaa aagctaaccc ttgatgcaaa agaaccttg     420 gacattaaaa ggaatatgtc aagccagcta tatataaaac cttgtcttgt tggtggttg     480 aaaaaatgac tctatgattg ttgttttggg tgcaatgaag aaattgtatt ctctcttgtc     540
tttgttgtgt gcactgttga ttccaccaac atgtttcaaa aaactatcct tgtgattcta     600
```

```
atttctaaat cacccgttca caaaaaatct ccacaaacat gcaaattgtc cttgaaaaga    660
taacatacaa gtagaaagca tcatcttttt tactatactc aagccaacta taaggcttaa    720
accatttagc tacaaatatc gatgcacacc tccggtgggg tgttgtggaa aagcatgtta    780
ttttggccga taagccccct ttacagtgta tcctcttcta attctattca gatcattaac    840
atcagctgtg attgacatcc tcttcccaag attagattca cgcaattgaa catcataaac    900
cacatcttca atgtcatcct cttcctatat attttcagat tattggcttg cttcgttctc    960
aatatcaggt tctatgaatg gacttctgtt gatgccacta ataatttgta gttgttgtgg   1020
aatataaatt gaacgggagc tcatggtgct atgaacttga ttggatgaga aattgttcta   1080
cagctccact tgctgctcaa cctaaataca tgcttggatt tcttcccagc tctagcacat   1140
aaagttttca aattaatgtt tccaccacat aaagttttga aatccacaaa tactttttt    1200 agtacatgaa cattttttcta atatacggtg aagattttc atatacaaac tgatcgtttt   1260
aatatatggt aaaaattggt gtaatatatg ctgaaatgtt ttcaaataca tattgaatat   1320
atttataata aatggtgagc atttctgtaa tacatgatga ccattttaaa aatacatatc   1380
gaacatttca taatatacga tgaacagttt tataatactc gatgaacata ttttggagtt   1440
ctgaacaatt ttttttcaaa aacacaagcc attttccagg aaaaaacaaa agcaaaagaa   1500
atgagaaacc caaaaacaa aaaagcaaag cagaacaaaa caaaacaaaa caaaacagag   1560
aaatctacac ggaaaatgaa acagaaaaag taaagaaaga acccgaactg ggccaggcaa   1620
tgtttgcaac ggcctcgctc ttcctgaaca agaaggtcag tccatgggct gcttccagta   1680
cacgggcctc gctgtgtggc aacacgccat gtaaatagttt tcgcgggaat ccaacgtcgg   1740
tctggtgact tctggtgcct accagaactc tccacaagct cccacaggac ccacgcagcc   1800
gtctgatcag atcagcacga agcacgaact ttgaagcgcg gcgatatttt ctctccccag   1860
cctccgcctc gcccgacgac gctgcgctgc agcaccattt caatttcaaa atcaaaatcg   1920
aaaacggaaa agctttctcg catcccgagg agaggcggtt acgcgcgcca gaggagcacg   1980
agagaggcca ccccaccca ccccgccctc acgtgccgcg ctcgcacccc ccgcggccgc   2040 atccggggccg tccgcgcgga cagctggccg cgccccaccc gaaccgacgc ccaggatcga   2100
gcgagagcgg cgcgcccgag gcttggctta gcgtccacgg ctcctccggc tatataaccc   2160
gcccgccacc cgctccccct ccggcattcc attccgccac cgcacccca ctccaccaca   2220 aaccctagcg agcgagcgag agggagagac cgccccgccc cgccg                  2265
```

<210> SEQ ID NO 5
<211> LENGTH: 628
<212> TYPE: DNA
<213> ORGANISM: Elytrigia elongata

<400> SEQUENCE: 5

```
gtggccgacc ccgaggccat ggtccgtcca gttgcagtag agtgctcgtc gtcttgttcc     60
gtttcatgct tgtcgccatt tgaggttcgt ttctgcagtc cggtcgaaga agacggtgga    120
ttttgagtag tagtagtagc tatcgttggc aggagtatgg agttcatgtg tcctcggtcg    180
cctagttttg gtctcaagta gtactgtctg tccgccgtgt ttgggtgttt gcgattcctc    240
tggttagatg aaccactgct atgtgatcga tcgatatgat ctgaatggaa tggatcaagt    300
tttgcgttct gctgatgatg tgatatgctt cttcgtatat actcatgctc gacctatcta    360
tgttctccca tttgaatttg tggagcaaca gtttggcatg cttttgctct gctatgaatg    420
aatgcttctt gcatgcatct tgtctttgct taatttgaac tgtagaacgg atgcagttct    480
```

| gatttcttca tatgcatatg ctctgtatgt gttcatctct tcgaatttat tatgtagcaa | 540 |
| cagtttgtag cttttcattc tgctatgaat gaatgcctct tgcatgttgt ctttgcttaa | 600 |
| tttgtactag cagaatgcag accttgcg | 628 |

<210> SEQ ID NO 6
<211> LENGTH: 1487
<212> TYPE: DNA
<213> ORGANISM: Artifical sequence
<220> FEATURE:
<221> NAME/KEY: misc_feature
<222> LOCATION: (1)..(1487)
<223> OTHER INFORMATION: ZmBT1-ZmAA fusion sequence

<400> SEQUENCE: 6

| atggcggcga caatggcagt gacgacgatg gtgacgagga gcaaggagag ctggtcgtca | 60 |
| ttgcaggtcc cggcggtggc attcccttgg aagccacgag gtggcaagac cggcggcctc | 120 |
| gagttccctc gccgggcgat gttcgccagc gtcggcctca acgtgtgccc gggcgtcccg | 180 |
| gcggggcgcg acccgcggga gcccgatccc aaggtcgtcc gggcggcctg cggcctggtc | 240 |
| caggcacaag tcctcttcca ggggtttaac tgggagtcgt gcaagcagca gggaggctgg | 300 |
| tacaacaggc tcaaggccca ggtcgacgac atcgccaagg ccggcgtcac gcacgtctgg | 360 |
| ctgcctccac cctcgcactc cgtctcgcca caaggctaca tgccaggccg cctatacgac | 420 |
| ctggacgcgt ccaagtacgg cacggcggcg gagctcaagt ccctgatagc ggcgttccac | 480 |
| ggcagggggcg tgcagtgcgt ggcggacatc gtcatcaacc accggtgcgc ggaaaagaag | 540 |
| gacgcgcgcg gcgtgtactg catcttcgag ggcgggactc ccgacgaccg cctggactgg | 600 |
| ggccccggga tgatctgcag cgacgacacg cagtactcgg acgggacggg gcaccgcgac | 660 |
| cgggcgaggg gttcgcggcg gcgcccgaca tcgaccacct caacccgcgc gtgcagcggg | 720 |
| agctctccgc ctggctcaac tggctcaggt ccgacgccgt ggggttcgac ggctggcgcc | 780 |
| tcgacttcgc caagggctac tcgccggccg tcgccagaat gtacgtggag agcacggggc | 840 |
| cgccgagctt cgtcgtcgcg gagatatgga actcgctgag ctacagcggg gacggcaagc | 900 |
| cggcgcccaa ccaggaccag tgccggcagg agctgctgga ctggacgcgg gccgtcggcg | 960 |
| ggccccgccat ggcgttcgac ttccccacca agggcctgct gcaggcgggc gtgcagggg | 1020 |
| agctgtggcg gctgcgcgac agctccggca acgcggccgg cctgatcggg tgggcgcccg | 1080 |
| agaaggccgt caccttcgtc gacaaccatg acaccgggtc gacgcagaag ctctggccgt | 1140 |
| tcccatccga caaggtcatg cagggctacg cctacatcct cacccatcca ggagtccct | 1200 |
| gcattttcta cgaccacatg ttcgactgga acctgaagca ggagatatcc acgctgtctg | 1260 |
| ccatcagggc gcggaacggc atccgcgccg ggagcaagct gcggatcctc gtggcggacg | 1320 |
| cggacgcgta cgtggccgtc gtcgacgaga aggtcatggt gaagatcggg acaaggtacg | 1380 |
| gcgtgagcag cgtggtcccg tcggatttcc accggcggc gcacggcaag gactactgcg | 1440 |
| tctgggagaa agcgagcctc cgcgtcccgg cggggcgcca cctctag | 1487 |

<210> SEQ ID NO 7
<211> LENGTH: 2736
<212> TYPE: DNA
<213> ORGANISM: Zea mays

<400> SEQUENCE: 7

| tgcaccggac actgtctggt ggcataccag acagtccggt gtgccagatc agggcaccct | 60 |

```
tcggttcctt tgctcctttg cttttgaacc ctaactttga tcgtttattg gtttgtgttg    120
aacctttatg cacctgtgga atatataatc tagaacaaac tagttagtcc aatcatttgt    180
gttgggcatt caaccaccaa aattatttat aggaaaaggt taaaccttat ttcccttca    240 atctccccct ttttggtgat tgatgccaac acaaaccaaa gaaatatat aagtgcagaa     300 ttgaactagt ttgcataagg taagtgcata ggttacttag aattaaatca atttatactt    360
ttacttgata tgcatggttg cttctttta ttttaacatt ttggaccaca tttgcaccac     420
ttgttttgtt ttttgcaaat cttttgtgaa attctttc aaagtcttt gcaaatagtc       480 aaaggtatat gaataagatt gtaagaagca ttttcaagat ttgaaattc tcccctgtt      540 tcaaatgctt ttcctttgac taaacaaaac tcccctgaa taaaattctc ctcttagctt     600
tcaagagggt tttaaataga tatcaattgg aaatatattt agatgctaat tttgaaaata    660
taccaattga aaatcaacat accaatttga aattaaacat accaatttaa aaaatttcaa    720
aaagtggtgg tgcggtcctt ttgctttggg cttaatattt ctccccctt ggcattaatc     780 gccaaaaacg gagactttgt gagccattta tactttctcc ccattggtaa atgaaatatg    840
agtgaaagat tataccaaat ttggacagtg atgcggagtg acggcgaagg ataaacgata    900
ccgttagagt ggagtggaag ccttgtcttc gccgaagact ccatttccct ttcaatctac    960
gacttagcat agaaatacac ttgaaaacac attagtcgta gccacgaaag agatatgatc   1020
aaaggtatac aaatgagcta tgtgtgtaat gtttcaatca aagttcgag aatcaagaat    1080 atttagctca ttcctaagtt tgctaaaggt tttatcatct aatggtttgg taaagatatc   1140
gactaattgt tctttggtgc taacataagc aatctcgata tcacccctt gttggtgatc    1200 cctcaaaaag tgataccgaa tgtctatgtg cttagtgcgg ctgtgttcaa cgggattatc   1260
cgccatgcag atagcactct cattgtcaca taggagaggg actttgctca atttgtagcc   1320
atagtcccta aggttttgcc tcatccaaag taattgcaca caacaatgtc ctgcggcaat   1380
atacttggct tcgcggtag aaagagctat tgagttttgt ttctttgaag tccaagacac    1440
cagggatctc cctagaaact gacaagtccc tgatgtgctc ttcctatcaa ttttacaccc   1500
tgcccaatcg gcatctgaat atcctattaa atcaaaggtg gatcccttgg ggtaccaaag   1560
accaaattta ggagtgtaaa ctaaatatct catgattctt ttcacggccc taaggtgaac   1620
ttccttagga tcggcttgga atcttgcaca catgcatata gaaagcatac tatctggtcg   1680
agatgcacat aaatagagta aagatcctat catcgaccgg tataccttt ggtctacgga    1740 tttacctccc gtgtcgaggt cgagatgccc attagttccc atgggtgtcc tgatgggctt   1800
ggcatccttc attccaaact tgttgagtat gtcttgaatg tactttgttt ggctgatgaa   1860
ggtgccatct tggagttgct tgacttgaaa tcctagaaaa tatttcaact tccccatcat   1920
agacatctcg aatttcggaa tcatgatcct actaaactct tcacaagtag atttgttagt   1980
agacccaaat ataatatcat caacataaat ttggcataca aacaaaactt ttgaaatggt   2040
tttagtaaag agagtaggca cggctttact gactctgaag ccattagtga taagaaaatc   2100
tcttaggcat tcataccatg ctgttggggc ttgcttgagc ccataaagcg cctttgagag   2160
tttataaaca tggttagggt actcactatc ttcaaagccg agaggttgct caacatagac   2220
ctattcaccc catttgatca cttttttggt ccttcaggat ctaatagtta tgtataattt   2280
agagtctctt gtttaatggc cagatatttc taattaatct aagaatttat gatatttttt   2340 aatttttat catgtctgat gagaattaac ataaaggctc aattgggtcc tgaattaata   2400
atagagtgaa aattaatcca gaggctctat tagaaccttc aattagtaat accaagatat   2460
```

```
atataagata gtagagtata gtttaaatgt tggcattgtt cattctttct tttgttattt    2520
aatttatgct ttccacggtg gttagtggtt acttctgaag ggtccaaata atgcatgaag    2580
agtttgagga caagaagtct gccctaaaaa tagcgatgca aaggcatggt gtccaagcca    2640
tacatatagc gcactaattt tatcagcaga acaatggtat ttataggtcc tagtgcccag    2700
gcaacaagag acacgaataa agcatcgatc acgaca                             2736
```

<210> SEQ ID NO 8
<211> LENGTH: 344
<212> TYPE: DNA
<213> ORGANISM: Zea mays

<400> SEQUENCE: 8

```
tgacaaagca gcattagtcc gttgatcggt ggaagaccac tcgtcagtgt tgagttgaat     60
gtttgatcaa taaaatacgg caatgctgta agggttgttt tttatgccat tgataataca    120
ctgtactgtt cagttgttga actctatttc ttagccatgc caagtgcttt tcttattttg    180
aataacatta cagcaaaaag ttgaaagaca aaaaaaaaaa ccccgaaca gagtgctttg     240 ggtcccaagc tactttagac tgtgttcggc gttcccccta aatttctccc cctatatctc    300
actcacttgt cacatcagcg ttctctttcc cctatatctc cacg                     344
```

<210> SEQ ID NO 9
<211> LENGTH: 711
<212> TYPE: DNA
<213> ORGANISM: Artifical sequence
<220> FEATURE:
<221> NAME/KEY: misc_feature
<222> LOCATION: (1)..(711)
<223> OTHER INFORMATION: mCherryW gene sequence

<400> SEQUENCE: 9

```
atggtgtcca agggcgagga ggacaacatg gccatcatca aggagttcat gcgcttcaag     60
gtgcacatgg agggctccgt gaacggccac gagttcgaga tcgagggcga gggcgagggc    120
cgcccctacg agggcaccca aaccgccaag ctcaaggtga ccaagggtgg ccccctcccc    180
ttcgcctggg acatcctctc cccacaattc atgtacggct ccaaggccta cgtgaagcac    240
cccgccgaca tccccgacta cctcaagctc tccttccccg agggcttcaa gtgggagcgc    300
gtgatgaact tcgaggacgg cggcgtggtg accgtgaccc aagactcctc cctccaagac    360
ggcgagttca tctacaaggt gaagctccgc ggcaccaact tccctccga cggccccgta    420 atgcaaaaga gaccatggg ctgggaggcc tcctccgagc ggatgtaccc cgaggacggc    480
gccctcaagg gcgagatcaa gcaaaggctc aagctcaagg acggcggcca ctacgacgcc    540
gaggtgaaga ccacctacaa ggccaagaag cccgtgcaac tccccggcgc ctacaacgtg    600
aacatcaagc tcgacatcac ctcccacaac gaggactaca ccatcgtgga gcaatacgag    660
cgcgccgagg ccgccactc caccggcggc atggacgagc tgtacaagtg a              711
```

<210> SEQ ID NO 10
<211> LENGTH: 1149
<212> TYPE: DNA
<213> ORGANISM: Artifical sequence
<220> FEATURE:
<221> NAME/KEY: misc_feature
<222> LOCATION: (1)..(1149)
<223> OTHER INFORMATION: CaMV35S enhancer-LTP2 promter

<400> SEQUENCE: 10

```
cgtcaacatg gtggagcacg acacgcttgt ctactccaaa aatatcaaag atacagtctc      60
agaagaccaa agggcaattg agacttttca acaaagggta atatccggaa acctcctcgg     120
attccattgc ccagctatct gtcactttat tgtgaagata gtggaaaagg aaggtggctc     180
ctacaaatgc catcattgcg ataaaggaaa ggccatcgtt gaagatgcct ctgccgacag     240
tggtcccaaa gatggacccc cacccacgag gagcatcgtg gaaaagaag acgttccaac     300 cacgtcttca aagcaagtgg attgatgtga tgaattcaac cgtctcttcg tgagaataac     360
cgtggcctaa aaataagccg atgaggataa ataaaatgtg gtggtacagt acttcaagag     420
gtttactcat caagaggatg cttttccgat gagctctagt agtacatcgg acctcacata     480
cctccattgt ggtgaaatat tttgtgctca tttagtgatg ggtaaatttt gtttatgtca     540
ctctaggttt tgacatttca gttttgccac tcttaggttt tgacaaataa tttccattcc     600
gcggcaaaag caaaacaatt ttattttact tttaccactc ttagctttca caatgtatca     660
caaatgccac tctagaaatt ctgtttatgc cacagaatgt gaaaaaaac actcacttat     720 ttgaagccaa ggtgttcatg gcatggaaat gtgacataaa gtaacgttcg tgtataagaa     780
aaaattgtac tcctcgtaac aagagacgga aacatcatga gacaatcgcg tttggaaggc     840
tttgcatcac ctttggatga tgcgcatgaa tggagtcgtc tgcttgctag ccttcgccta     900
ccgcccactg agtccgggcg gcaactacca tcggcgaacg acccagctga cctctaccga     960
ccggacttga atgcgctacc ttcgtcagcg acgatggccg cgtacgctgg cgacgtgccc    1020
ccgcatgcat ggcggcacat ggcgagctca gaccgtgcgt ggctggctac aaatacgtac    1080
cccgtgagtg ccctagctag aaacttacac ctgcaactgc gagagcgagc gtgtgagtgt    1140
agccgagta                                                            1149

<210> SEQ ID NO 11
<211> LENGTH: 310
<212> TYPE: DNA
<213> ORGANISM: Solanum tuberosum

<400> SEQUENCE: 11
ctagacttgt ccatcttctg gattggccaa cttaattaat gtatgaaata aaaggatgca      60
cacatagtga catgctaatc actataatgt gggcatcaaa gttgtgtgtt atgtgtaatt     120
actagttatc tgaataaaag agaaagagat catccatatt tcttatccta aatgaatgtc     180
acgtgtcttt ataattcttt gatgaaccag atgcatttca ttaaccaaat ccatatacat     240
ataaatatta atcatatata attaatatca attgggttag caaaacaaat ctagtctagg     300
tgtgttttgc                                                            310
```

FERTILITY RESTORATION GENE IN WHEAT AND USES THEREOF

SEQUENCE LISTING

The instant application contains a Sequence Listing, which has been submitted electronically in ASCII format and is hereby incorporated by reference in its entirety. Said ASCII copy was created on 15 Apr. 2019, is named "PN96798BDRJ_amended_Sequence_List.txt", is 19568 bytes in size, and contains a sequence listing identical to the sequence listing filed in the corresponding international application no. PCT/CN2017/094012 filed on 24 Jul. 2017.

TECHNICAL FIELD

The invention belongs to the field of plant biotechnology, particularly relates to the cloning of a plant recessive genic male sterility gene, and a propagation method of a male sterile line thereof and uses in hybrid breeding. More particularly, it relates to the cloning of a recessive genic male sterile gene and a promoter thereof, and uses thereof in the hybrid breeding.

BACKGROUND

Hybrid vigor is a universal phenomenon in the living nature, and hybrid breeding is a main route to breed new varieties, and is one of the most important method for modern breeding works. In contrast to rice, corn, broomcorn, etc., the research on wheat hybrid vigor utilization is hysteretic relatively. The rate of yield gain in wheat has stagnated, even declined over the last decade. The wheat is a self-pollination crop, a core problem of the wheat hybrid vigor utilization is to develop a wheat hybrid seed production system. For this purpose, a plurality of domestic and overseas scientists have made great efforts and achieved a series of significant results in recent fifty years. The research of the wheat hybrid vigor utilization mainly focused on: utilization of the nucleo-cytoplasmic interaction male sterility (three-line system, CMS), utilization of chemically induced male sterility (using chemical hybridizing agents [CHAS]) and utilization of photo-thermo-sensitive genic male sterility (two-line system). The three-line system has been difficult to be used in large scale due to the difficulty of breeding, the negative cytoplasmic effort from sterile line and the lack of effective fertility-restoring genes. CHA, once considered as the most hopeful wheat hybrid seed production system, has suffered from problems of instability, high-cost and toxicity. Although the two-line system, based on the photo-thermo-sensitive genic male sterility, is low-cost, the fertility of the male sterile line can be restored by any normal cultivars, and broader genetic resources can be explored for strong heterosis, the two-line system is also faced with two key problems. Firstly, its sterility is influenced by the instable environmental factors; secondly, a limited number of photo-thermo-sensitive genic male sterile lines have been got.

For the utilization of crop hybrid vigor, the sterility of the recessive genic male sterile mutants (GMS) is easily restored, but is not easily maintained. In contrast to the cytoplasmic male sterile hybrid wheat system (CMS), the recessive genic male sterile mutant has the following advantages while used for the hybrid wheat development: 1) there isn't negative cytoplasmic effort from sterile line and the heterosis of hybrid F1 is more remarkable; 2) the fertility of sterile line is restored more completely by restorer line, and the hybrid F1 has better fertility; 3) the male sterility is controlled by a single recessive genic gene and the fertility of the male sterile line can be restored by any germplasms with its wild-type gene, which provides broader choices of germplasms as paternal lines to breed hybrids. However, the mass production of genic sterile line seeds is difficult through conventional methods. So, in the current situation of utilization of the wheat hybrid vigor, establishing of an efficient wheat hybrid breeding systems is one of the key factors for the successful application of the hybrid wheat.

Because of the genetic characteristics, there is not a complete restorer line and a complete maintenance line of wheat dominant genic male sterile line, such as 'Taigu genic male-sterile wheat' (called MS2) discovered in China in 1972. So the wheat dominant genic male sterile line is only suitable for conventional recurrent selection breeding and backcross breeding, and cannot be used as a parent in hybrid wheat breeding. However, all the F1 generation plants of recessive genic male sterile material hybridized with any normal material are male-fertile. In other words, any normal material is the restorer line of the recessive genic male sterile material. Therefore, the recessive genic male sterile line can be applied to the new generation of a wheat hybrid breeding technology, so long as the problem of marking and effective maintenance of genic male sterile line are solved.

The wheat genome is huge (17 Gb), which is about 5 times human genome, 40 times rice genome, and 100 times *Arabidopsis* genome. The composition of wheat genome is extremely complicated. There are three chromosome set (A, B, and D) with partial homologous relation in wheat genome and each chromosome set has 7 pairs of chromosomes, so wheat genome has totally 21 pairs of chromosomes and is a typical allohexaploid (Zhang Z B. et al., 2002), and has about 75% simple repetitive sequences (Rachel B. et al., 2012; IWGSC. 2014). In recent years, although the genome sequencing of wheat and sibling species thereof has made great progress, up to now, no complete reference genomic sequence has been published yet (Vogel J P, et al., 2010; The International Barley Genome Sequencing Consortium, 2012; Rachel B, et al., 2012; Ling H Q, et al., 2013; Jia J, et al., 2013; IWGSC, 2014). Such complex genome makes it extremely difficult to study functional genes, so far, there are only a few examples of successful cloning of genes from wheat mutants in an international scope.

Fertility Restoration Gene FRG1 is successfully cloned by flow cytometry and high-throughput sequencing in this invention. The FRG1 gene can completely restore the male fertility of Lanzhou genic male sterile mutant or an allelic mutant thereof, which lays a foundation for the construction of a new wheat hybrid breeding technology system, meanwhile, which provides more possibilities to solve the technical bottlenecks of "three-lines" and "two-lines" hybridization technology of wheat, such as unstable fertility of sterile lines, limited resources for hybrid variety, the complexity of seed production technology and the high cost of seed production. The gene and the propagation and maintenance method of sterile line have important significance and application value for hybrid breeding in wheat.

SUMMARY

All references mentioned herein are incorporated into this application by citation.

Unless otherwise specified, all technical and scientific terms used herein have the same meanings as those commonly understood by those of ordinary skill in the art of the invention. Unless otherwise specified, the techniques used or mentioned herein are standard techniques publicly known by those of ordinary skill in the art. Materials, methods and examples are only used for explaining, and are not intended to limit.

The invention provides a Fertility restoration gene1 (FRG1), and a nucleotide sequence of the fertility restoration gene is selected from one of the following groups of sequences:

(a) a nucleotide sequence as shown in SEQ ID NO: 1 or 2;

(b) a nucleotide sequence coding an amino acid sequence as shown in SEQ ID NO: 3;

(c) a DNA sequence capable of hybridizing with the sequence in (a) or (b) under stringent conditions; or (d) a DNA sequence having 80% (preferably at least 85%) similarity with the sequence of (a)-(c) and having a fertility restore function; or (e) a DNA sequence complemented with any one of the sequence of (a)-(d).

It is to be noted by those skilled in the art that the fertility restoration gene of the invention further includes a homologous gene sequence which has a high homology with the nucleotide sequence or a protein sequence of the FRG1 gene, and also has fertility regulation or restoration function. The homologous gene with the high homology and the fertility regulation function includes a DNA sequence capable of hybridizing with the sequence as shown in SEQ ID NO: 1 or 2, or a nucleotide sequence coding an amino acid sequence has 85% similarity or more with the protein amino acid sequence as shown in SEQ ID NO: 3. The 'stringent conditions' used herein are well known, for example, hybridizing for 12-16 hours in 53-60 DEG C. in hybridization solution comprising 400 mM NaCl, 40 mM PIPES (pH 6.4) and 1 mM EDTA, and washing for 15-60 minutes in 62-68 DEG C with a washing liquid containing 0.5×SSC and 0.1% of SDS.

The above homologous gene further includes a DNA sequence which has at least 80%, 85%, 90%, 95%, 98% or 99% sequence similarity with full length sequence as shown in SEQ ID NO: 1 or 2 and has the fertility regulation function, and can be separated and acquired from any plant. A percentage of the sequence similarity may be obtained by a public bioinformatics algorithm, including a Myers-Miller algorithm, a Needleman-Wunsch algorithm for global alignment, a Smith-Waterman algorithm for local alignment, a Lipman-Pearson algorithm for similarity search, and a Karlin-Altschul statistics. It is well known to those skilled in the art.

The invention further provides an expression cassette, the expression cassette comprises a nucleotide sequence of the fertility restoration gene disclosed by the invention, and the nucleotide sequence of the fertility restoration gene is selected from one of the following groups of sequences:

(a) a nucleotide sequence as shown in SEQ ID NO: 1 or 2;

(b) a nucleotide sequence coding an amino acid sequence as shown in SEQ ID NO: 3;

(c) a DNA sequence capable of hybridizing with the sequences in (a) or (b) under stringent conditions; or (d) a DNA sequence having 80% (preferably at least 85%) similarity with the sequence of (a)-(c) and having a fertility restoration function; or (e) a DNA sequence complemented with any one of the sequence of (a)-(d).

Specifically, the fertility restoration gene in the above expression cassette is further operably connected with a promoter which can drive the expression of the fertility restoration gene, the promoter includes, but not limit to, a constitutive expression promoter, an inducible promoter, a tissue-specific promoter, or a spatiotemporal-specific promoter. More specifically, the promoter is a pollen-specific promoter. Preferably, a nucleotide sequence of the pollen-specific promoter is shown in SEQ ID NO: 4.

The above expression cassette of the invention further includes a pollen inactivation gene, the pollen inactivation gene can disturb the function or formation of the male gamete comprising the pollen inactivation gene in a plant. The pollen inactivation gene includes, but not limited to, a barnase gene, an amylase gene, a DAM methylase gene and the like. More specifically, the pollen inactivation gene is a corn α-amylase gene, preferably a nucleotide sequence of the pollen inactivation gene is shown in SEQ ID NO: 6.

The above expression cassette of the invention further includes a screening gene, the screening gene can be used for screening a plant, a plant tissue cell or a vector comprising the expression cassette. The screening gene includes, but not limited to, an antibiotic-resistance gene, or a herbicide-resistance gene, or a fluorescent protein gene and the like. Specifically, the screening gene includes, but not limited to, a chloramphenicol-resistance gene, a hygromycin-resistance gene, a streptomycin-resistance gene, a miramycin-resistance gene, a sulfonamide-resistance gene, a glyphosate-resistance gene, phosphinothricin-resistance gene, a bar gene, a red fluorescence gene DsRED, a mCherry gene, a cyan fluorescence protein gene, a yellow fluorescence protein gene, a luciferase gene, a green fluorescence protein gene and the like.

The invention further discloses a method for regulating plant fertility, the method comprises through transforming the fertility restoration gene to a Lanzhou genic male sterile mutant (Zhou Kuangji and the like, 1996) or an allelic mutant thereof, and restoring the male fertility of the Lanzhou genic male sterile mutant or the allelic mutant thereof, herein the nucleotide sequence of the fertility restoration gene is selected from one of the following groups of sequences:

(a) a nucleotide sequence as shown in SEQ ID NO: 1 or 2;

(b) a nucleotide sequence coding an amino acid sequence as shown in SEQ ID NO: 3;

(c) a DNA sequence capable of hybridizing with the nucleotide sequence in (a) or (b) under stringent conditions; or (d) a DNA sequence having 80% (preferably at least 85%) similarity with the nucleotide sequence of (a)-(c) and having a fertility restoration function; or (e) a DNA sequence complemented with any one of the nucleotide sequence of (a)-(d).

The Lanzhou genic male sterile mutant in the invention is also named as a Lanzhou genic male sterility or a Lanzhou nuclear sterile line or a Lanzhou nuclear sterile mutant.

The invention further discloses a method for maintaining a male sterile line, the method comprises using the Lanzhou genic male sterile mutant or the allelic mutant thereof as a transformation acceptor material, and transforming three closely-linked target genes to the acceptor plant of the sterile mutant. The three target genes are the fertility restoration gene FRG1, the pollen inactivation gene and a screening gene respectively. The fertility restoration gene FRG1 may restore the fertility of a sterile transformation acceptor, the pollen inactivation gene may inactivate pollen comprising a transformed exogenous gene, namely the fertilization ability is lost; the screening gene may be used for sorting transgenic seeds or tissues from non-transgenic seeds or tissues, the sorted non-transgenic seeds are used as the sterile line for producing the hybrid seeds, and the transgenic seeds are used as the maintenance line for producing the sterile line continuously and stably.

In the invention, the Lanzhou genic male sterile mutant or the allelic mutant thereof may be named as a sterile line or a male sterile line or a Lanzhou genic male sterile line, or an allelic sterile line.

In the above method for maintaining the male sterile line, the pollen inactivation gene includes, but not limited to, a barnase gene, an amylase gene, DAM methylase gene and the like. More specifically, the pollen inactivation gene is a corn α-amylase gene Zm-AA, preferably a nucleotide sequence of the pollen inactivation gene is shown in SEQ ID NO: 6. The pollen inactivation gene is connected with a male gamete-specific promoter. More specifically, the male gamete-specific promoter includes, but not limited to, a PG47 promoter, a Zm13 promoter and the like. The screening gene may be used for screening plants or vectors comprising the expression cassette. The screening gene includes, but not limited to, an antibiotic-resistance gene, or a herbicide-resistance gene, or a fluorescent protein gene and the like. Specifically, the screening gene includes, but not limited to, a chloramphenicol-resistance gene, a hygromycin-resistance gene, a streptomycin-resistance gene, a miramycin-resistance gene, a sulfonamide-resistance gene, a glyphosate-resistance gene, a phosphinothricin-resistance gene, a bar gene, a red fluorescence gene DsRED, a mCherry gene, a cyan fluorescence protein gene, a yellow fluorescence protein gene, a luciferase gene, a green fluorescence protein gene and the like.

More specifically, the invention further discloses a method for propagating the male sterile line, the method includes the following steps:

(a) transforming the following vector to a Lanzhou genic male sterile line or the allelic sterile line thereof to obtain a maintenance line comprising the following vector, the vector comprises: a fertility restoration gene FRG1, the fertility restoration gene FRG1 can restore the male fertility of the Lanzhou genic male sterile line or the allelic sterile line thereof; and a pollen inactivation gene, expression of the pollen inactivation gene can disturb the function or formation of the male gamete with the pollen inactivation gene in a plant, so a fertile male gamete in the plant does not comprise the vector; and a screening gene, the screening gene can be used for sorting transgenic seeds or tissues from non-transgenic seeds or tissues.

(b) self-pollinating a maintenance line plant transformed with the above vector, and meanwhile producing seeds of the Lanzhou genic male sterile line or the allelic sterile line thereof not comprising the vector, and seeds of the maintenance line comprising the vector; or pollinating pollen grains of the maintenance line plant to a plant of the Lanzhou genic male sterile line or the allelic sterile line thereof to propagate seeds of the Lanzhou genic male sterile line or the allelic sterile line thereof.

In the above method for propagating the male sterile line, the pollen inactivation gene includes, but not limited to, a barnase gene, an amylase gene, a DAM methylase gene and the like. More specifically, the pollen inactivation gene is a corn α-amylase gene Zm-AA, preferably, a nucleotide sequence of the pollen inactivation gene is shown in SEQ ID NO: 6. The pollen inactivation gene is connected with a male gamete-specific promoter. More specifically, the male gamete-specific promoter includes, but not limited to, a PG47 promoter, a Zm13 promoter and the like. The screening gene can be used for selecting plants or vectors comprising the expression cassette. The screening gene includes, but not limited to, an antibiotic-resistance gene, or a herbicide-resistance gene, or a fluorescent protein gene and the like. Specifically, the screening gene includes, but not limited to, a chloramphenicol-resistance gene, a hygromycin resistant gene, a streptomycin-resistance gene, a miramycin-resistance gene, a sulfonamide-resistance gene, a glyphosate-resistance gene, a phosphinothricin-resistance gene, a bar gene, a red fluorescence gene DsRED, a mCherry gene, a cyan fluorescence protein gene, a yellow fluorescence protein gene, a luciferase gene, a green fluorescence protein gene and the like.

The invention further discloses a method for producing a maintenance line, the method includes the following steps:

(a) transforming the following vector to the Lanzhou genic male sterile line or the allelic sterile line thereof, so the maintenance line is acquired, the vector comprises a fertility restoration gene FRG1, the fertility restoration gene FRG1 can restore the male fertility of the Lanzhou genic male sterile line or the allelic sterile line thereof; and a pollen inactivation gene, the expression of the pollen inactivation gene can disturb the function or formation of the male gamete comprising the pollen inactivation gene in a plant, so a fertile male gamete generated in the plant does not comprise the vector; and a screening gene, the screening gene can be used for sorting transgenic seeds from non-transgenic seeds.

(b) self-pollinating a maintenance line plant transformed with the above vector, and meanwhile producing seeds of the Lanzhou genic male sterile line or allelic sterile line thereof not comprising the vector, and seeds of maintenance line comprising the vector; or pollinating pollen grains of the maintenance line plant to a plant of the Lanzhou genic male sterile line or the allelic sterile line thereof to propagate seeds of the Lanzhou genic male sterile line or the allelic sterile line thereof.

In the above method for producing the maintenance line, the pollen inactivation gene includes, but not limited to, a barnase gene, an amylase gene, a DAM methylase gene and the like. More specifically, the pollen inactivation gene is a corn α-amylase gene Zm-AA, preferably, a nucleotide sequence of the pollen inactivation gene is shown in SEQ ID NO: 6. The pollen inactivation gene is connected with a male gamete-specific promoter. More specifically, the male gamete-specific promoter includes, but not limited to, a PG47 promoter, a Zm13 promoter and the like. The screening gene may be used for screening plants or vectors comprising the expression cassette. The screening gene includes, but not limited to, an antibiotic-resistance gene, or a herbicide-resistance gene, or a fluorescent protein gene and the like. Specifically, the screening gene includes, but not limited to, a chloramphenicol-resistance gene, a hygromycin resistant gene, a streptomycin-resistance gene, a miramycin-resistance gene, a sulfonamide-resistance gene, a glyphosate-resistance gene, a phosphinothricin-resistance gene, a bar gene, a red fluorescence gene DsRED, a mCherry gene, a cyan fluorescence protein gene, a yellow fluorescence protein gene, a luciferase gene, a green fluorescence protein gene and the like.

The invention further discloses a method for propagating the maintenance line. the method includes the following steps:

(a) transforming the following vector to a Lanzhou genic male sterile line or the allelic sterile line thereof to obtain a maintenance line comprising the vector, the vector comprises: a fertility restoration gene FRG1, the fertility restoration gene FRG1 can restore the male fertility of the Lanzhou genic male sterile line or the allelic sterile line thereof; and a pollen inactivation gene, expression of the pollen inactivation gene can disturb the function or formation of a male gamete comprising the pollen inactivation gene in a plant, so a fertile male gamete generated in the plant does not comprise the vector; and a screening gene, the screening gene can be used for sorting transgenic seeds from non-transgenic seeds; and (b) self-pollinating maintenance line plants transformed with the above vector to obtain seeds of the Lanzhou genic male sterile line or the allelic sterile line thereof without the vector and seeds of the maintenance line with the vector at a ratio of 1:1.

The invention further discloses a method for producing seeds, the method includes the following steps:

(a) transforming the following vector to a Lanzhou genic male sterile line or a allelic sterile line thereof to obtain a maintenance line, the vector comprises: a fertility restoration gene FRG1, the fertility restoration gene FRG1 can restore the male fertility of the Lanzhou genic male sterile line or the allelic sterile line thereof; and a pollen inactivation gene, expression of the pollen inactivation gene can disturb the function or formation of a male gamete comprising the pollen inactivation gene in a plant, so a fertile male gamete generated in the plant does not comprise the vector;

(b) self-pollinating maintenance line plants transformed with the above vector; and (c) seeds of the Lanzhou genic male sterile line or the allelic sterile line thereof without the vector and seeds of the maintenance line with the vector are obtained.

In the above method for propagating or maintaining the male sterile line, the method for producing or propagating the maintenance line, and the method for producing seeds and the like of the invention, the step (a) may also be: introducing a vector comprising the fertility restoration gene FRG1, the pollen inactivation gene and the screening gene to a normal plant, after obtaining transgenic plants with the vector, crossing the transgenic plants with the Lanzhou genic male sterile line or the allelic sterile line thereof, and obtaining maintenance line plants comprising the vector and homozygous Lanzhou genic male sterile mutation or allelic mutation thereof through directed selection.

In the above method for propagating or maintaining the male sterile line, the method for producing or propagating the maintenance line, and the method for producing seeds and the like of the invention, the nucleotide sequence of the fertility restoration gene is selected from one of the following groups of sequences:

(a) a nucleotide sequence as shown in SEQ ID NO: 1 or 2;

(b) a nucleotide sequence coding an amino acid sequence as shown in SEQ ID NO:3;

(c) a DNA sequence capable of hybridizing with the nucleotide sequences in (a) or (b) under stringent conditions; or (d) a DNA sequence having 80% (preferably at least 85%) similarity with the nucleotide sequence of (a)-(c) and having a fertility restoration function; or (e) a DNA sequence complemented with any one of the nucleotide sequence of (a)-(d).

The above fertility restoration gene FRG1 may be further operably connected with a pollen-specific promoter, which drives the FRG1 gene specifically expressed in the plant pollen. The pollen-specific promoter is selected from one of groups consisting of promoters of fertility regulation genes of MS26, NP1, MSP1, PAIR1, PAIR2, ZEP1, MELL, PSS1, TDR, UDT1, GAMYB4, PTC1, AP15, WDA1, CYP704B2, MS22, DPW, MADS3, OSCE, RIP1, CSA, AID1, 5126, Ms45 and the like. More specifically, the nucleotide sequence of the pollen-specific promoter is shown in SEQ ID NO: 4. The above fertility restoration gene FRG1 may also be operably connected with a terminator, the terminator may be a terminator of any gene disclosed publicly, specifically, a nucleotide sequence of the terminator is shown in SEQ ID NO: 5. In the above method for propagating or maintaining the male sterile line, the method for producing or propagating the maintenance line, and the method for producing seeds and the like of the invention, the pollen inactivation gene includes, but not limited to, a barnase gene, an amylase gene, a DAM methylase gene and the like. More specifically, the pollen inactivation gene is a corn α-amylase gene Zm-AA, preferably a nucleotide sequence of the pollen inactivation gene is shown in SEQ ID NO: 6. The pollen inactivation gene is connected with a male gamete-specific promoter. More specifically, the male gamete-specific promoter includes, but not limited to, a PG47 promoter, a Zm13 promoter and the like.

In the above method for propagating or maintaining the male sterile line, the method for producing or propagating the maintenance line, and the method for producing seeds and the like of the invention, the screening gene includes, but not limited to, an antibiotic-resistance gene, or a herbicide-resistance gene, or a fluorescent protein gene and the like. Specifically, the screening gene includes, but not limited to, a chloramphenicol-resistance gene, a hygromycin resistant gene, a streptomycin-resistance gene, a miramycin-resistance gene, a sulfonamide-resistance gene, a glyphosate-resistance gene, a phosphinothricin-resistance gene, a bar gene, a red fluorescence gene DsRED, a mCherry gene, a cyan fluorescence protein gene, a yellow fluorescence protein gene, a luciferase gene, a green fluorescence protein gene and the like.

The invention further provides a pollen-specific promoter, a nucleotide sequence of the promoter is shown in SEQ ID NO: 4. The SEQ ID NO: 4 was inserted into a vector, connecting with a reporter gene GUS. The rice and wheat are transformed with the vector, and the activity and the expression pattern of GUS are detected and analyzed in transgenic plants. Through GUS staining analysis on roots, stems, leaves and flowers of the transgenic plants, it is discovered that the promoter provided by the invention drives the expression of GUS gene in the plant pollen. It shows that the SEQ ID NO: 4 provided by the invention is a pollen-specific promoter.

The pollen-specific promoter provided by the invention comprises a nucleotide sequence as shown in SEQ ID NO: 4 of the sequence listing, or comprises a nucleotide sequence which has 90% similarity with the nucleotide sequence as shown in SEQ ID NO: 4, or comprises a fragment with 500 and more than 500 continuous nucleotides derived from SEQ ID NO: 4 and can drive the nucleotide sequence operably connected with thereof to be expressed in the plant pollen. The expression vector comprising the above sequence, the transgenic cell line and host bacteria and the like fall within the protection scope of the invention. A primer pair for amplifying any one of nucleotide fragments from the SEQ ID NO: 4 promoters disclosed by the invention also falls within the protection scope of the invention.

The 'promoter' of the invention is a DNA regulatory region, generally comprising a TATA box which may guide RNA polymerase II to initiate RNA synthesis at the appropriate transcription initiation site of a specific coding sequence. The promoter may further comprise other recognition sequences, the recognition sequences are generally located at the upstream or 5'-end of the TATA box, generally called as upstream promoter elements for regulating the transcription efficiency. It is known for those skilled in the art that although the nucleotide sequence for the promoter disclosed herein has been identified, the separation and identification of the other regulatory elements located in the upstream of the TATA box of the specific promoter region identified by the invention also fall within the scope of the invention. So the promoter region disclosed herein is generally further defined as sequences comprising an upstream regulatory element, such as enhancers and the like for regulating the tissue-specific and time-specific expression function of the coding sequence. In the same way, the promoter element showing tissue-specific expression (for example, male tissue-specific) may be identified and separated, and used together with other core promoter, to be verified the preferential expression in the male tissue. The core promoter is a minimal sequence required for the initiation of transcription, for example, the sequence named as the TATA box, which usually exists in the promoter of a protein-coding gene. So, optionally, the upstream promoter of the FRG1 gene may be used in association with its own core promoter or the core promoter from other sources.

The core promoter may be any known core promoter, such as a cauliflower mosaic virus 35S or 19S promoter (U.S. Pat. No. 5,352,605), a ubiquitin promoter (U.S. Pat. No. 5,510, 474), a IN2 core promoter (U.S. Pat. No. 5,364,780) or a figwort mosaic virus promoter.

The functions of the gene promoter may be analyzed through the following method: operably connecting the promoter sequence with a reporter gene to form a transformable vector, and then transforming the vector into a plant, confirming the expression specificity by observing the expression pattern of the reporter gene in each tissue organ of the transgenic offspring plants; or sub-cloning the above vector to an expression vector for a transient expression experiment, then detecting the function of the promoter or the regulatory region thereof through the transient expression experiment.

The selection of the appropriate expression vector for testing function of the promoter or the regulatory region depends on a host and a method for introducing the expression vector to the host, this type of the method is well known for those of ordinary skill in the art. For eukaryotes, the region in the vector includes regions for controlling the transcription initiation and controlling the processing. These regions are operably connected to a reporter gene, the reporter gene includes YFP, UidA, GUS or luciferase genes. The expression vector comprising a presumed regulatory region in the genome fragment may be introduced to a whole tissue, for example, pollen at certain developmental stage, or introduced to a callus for functional verification.

In addition, the promoter of the invention may also be connected with the nucleotide sequence other than FRG1 gene, to express the other heterologous nucleotide sequence. The nucleotide sequence of the promoter in the invention and the fragment thereof and the variant may be assembled in an expression cassette with the heterologous nucleotide sequence, and used for expression in a target plant, more specifically, expression in a male organ of the plant. The expression cassette has suitable restriction enzyme cleavage sites, which are used for insertion of the promoter and the heterologous nucleotide sequence. These expression cassettes may be used for gene manipulation on any plant, to obtain an expected corresponding phenotype.

The pollen-specific promoter disclosed by the invention may be used for driving the expression of the following heterologous nucleotide sequence to obtain the male sterile transgenic plants, the heterologous nucleotide sequence may code an enzyme promoting the degradation of carbohydrate or a modification enzyme, a amylase, a debranching enzyme and a pectinase, more specifically, for example, a barnase gene, a corn α-amylase gene, an auxin gene, a rot B gene, a cytotoxin gene, a diphtheria toxin gene, a DAM methylase gene, or a dominant male sterile gene.

In some embodiments, the nucleotide sequence mentioned in the invention is operably connected to the downstream of the promoter of the invention, the 'nucleotide sequence' may be a structural gene, a regulator gene, an antisense gene of the structural gene, an antisense gene of the regulator gene or the gene of a small RNA capable of disturbing endogenous gene expression.

The invention further provides a transcription terminator sequence, a nucleotide sequence of the transcription terminator is shown in SEQ ID NO: 5, and has a function of terminating the gene transcription.

The invention further provides an expression cassette, a vector or an engineering strain, which comprises the pollen-specific promoter SEQ ID NO: 4 provided by the invention. Specifically, the nucleotide sequence of the fertility restoration gene FRG1 provided by the invention may be constructed at the downstream of the promoter SEQ ID NO: 4 provided by the invention, to drive the fertility restoration gene to be expressed in the acceptor plant of transformation.

The pollen-specific promoter provided by the invention may be used for the specific expression of the exogenous gene in the pollen, so the negative effect caused by the continuous expression of the exogenous gene in the other tissues of plants is avoided. The pollen-specific promoter also may be used for the functional analysis and identification of a plant pollen growth and development related gene; may also be used for the construction of the male sterile line and the maintenance line; and may be applied to a pollen abortion experiment, so a bio-safety problem caused by plant transgenic flow or pollen escape is avoided, and the pollen-specific promoter has an important significance to the creation of the plant male sterile line and the maintenance line.

The nucleotide sequence and the promoter sequence or the expression cassette of the FRG1 gene provided by the invention may be inserted into a vector, a plasmid, a yeast artificial chromosome, a bacterial artificial chromosome or any other vectors suitable for transformation into a host cell. Preferable host cell is a bacterial cell, especially the bacterial cell for cloning or storing polynucleotide, or for transforming a plant cell, for example, *Escherichia coli*, *Agrobaterium tumefaciens* and *Agrobacterium rhizogenes*. When the host cell is a plant cell, the expression cassette or the vector may be inserted into the genome of the transformed plant cell. The insertion may be either a site-specific insertion or a random insertion.

The methods of transforming or introducing the nucleotide sequence, the vector or the expression cassette into the plant, or transforming the plant in the invention are conventional transgenic methods through which the nucleotide sequence, the vector or the expression cassette is transformed into the acceptor cell or the acceptor plant. Any transgenic methods known by those skilled in the art of plant biotechnological may be used for transforming a recombinant expression vector into the plant cell to produce the transgenic plant of the invention. The transformation method may include direct and indirect transformation methods. The suitable direct method includes polyethylene glycol-induced DNA intake, lipidosome mediated transformation, particle bombardment, electroporation, and microinjection. The transformation method also includes an *Agrobacterium*-mediated plant transformation method and the like.

Compared with the prior art, the invention has the following beneficial effects: the invention provides a fertility restoration gene FRG1 and a promoter thereof, and methods using the gene in propagating and maintaining of a Lanzhou genic male sterile line or an allelic sterile line thereof. The fertility restoration gene, the fertility maintenance of the wheat recessive genic male sterile line and the propagation of the sterile line provided by the invention have an important value of production popularization and application to the wheat hybrid production. The fertility restoration gene provided by the invention is capable of solving the propagation and maintenance problems of the Lanzhou genic male sterile line or the allelic sterile line thereof, and has a great significance to break through and improve the existing "three-lines" and "two-lines" hybridization technology.

REFERENCES

Zhou Kuangji, Zhou Wenlin, Wang Shuying (1996) The establishment of wheat 4E-ms male genic sterile and maintenance lines. Agricultural Science in China 29:93
The International Barley Genome Sequencing Consortium (2012) A physical, genetic and functional sequence assembly of the barley genome. Nature 491:711
The International Wheat Genome Sequencing Consortium (IWGSC) (2014) A chromosome-based draft sequence of the hexaploid bread wheat (*Triticum aestivum*) genome. Science 345:1251788
Jia J, Zhao S, Kong X, et al. (2013) *Aegilops tauschii* draft genome sequence reveals a gene repertoire for wheat adaptation. Nature 496:91
Ling H Q, Zhao S, Liu D, et al. (2013) Draft genome of the wheat A-genome progenitor *Triticum urartu*. Nature 496: 87
Rachel B, Manuel S, Matthias P, et al. (2012) Analysis of the bread wheat genome using whole-genome shotgun sequencing. Nature 491:705
Vogel J P, Garvin D F, Mockler T C, et al. (2010) Genome sequencing and analysis of the model grass *Brachypodium distachyon*. Nature 463:763
Zhang Z B, Xu P (2002) Reviewed on wheat genome. Hereditas 24:389

DETAILED DESCRIPTION OF THE EMBODIMENTS

The embodiments of the invention are described below in detail, the embodiments are implemented with the technical scheme of the invention as a precondition, and detailed implementation and specific operation process are provided, but the protection scope of the invention is not limited to the following embodiments.

Embodiment 1. Breeding of 4AgS-Ms Alien Ditelosomic Addition Line

Lanzhou genic male sterile mutant was discovered in a F4-generation population of hybrids between spring wheat varieties. Lanzhou genic male sterile mutant was hybridized with 9 wheat varieties including Chinese spring, and all F1-generation plants were selfing. The F2-generation plants were observed and the segregation ratio of sterile and fertile plants accorded with the ratio of 1:3, which indicated that Lanzhou genic male sterile mutant is a typical recessive mutant controlled by a single-gene (Zhou Kuanji et. al., 1996).

Blue grain alien disomic addition line is a wheat line in which two 4Ag chromosomes from *Thinopyrum ponticum* have been introduced into wheat genome, and the grains of alien disomic addition line are blue because of the blue-grain gene Ba on 4Ag chromosome. Pollen grains of the blue grain alien disomic addition line were pollinated to the Lanzhou genic male sterile mutant, so that light blue hybrid seeds were obtained and all the F1 plants were normally fruited. Through targeted breeding, a line named as 4Ag-ms alien monosomic addition line was obtained, which had homozygous mutation of Lanzhou genic male sterile mutant and one 4Ag chromosome from *Thinopyrum ponticum*. The grains of the line were blue, and the plants of the line were self-fertile, indicating that the 4Ag chromosome from *Thinopyrum ponticum* contains a fertility restoration gene.

Figure 1:
FIG. 1 shows GISH analysis of 4AgS-ms alien ditelosomic addition line. The genomic DNA of *Thinopyrum ponticum* was used as a probe for hybridizing, the red fluorescence signal indicated 4AgS chromosome; and chromosomes were stained with DAPI (blue).
Figure 2:
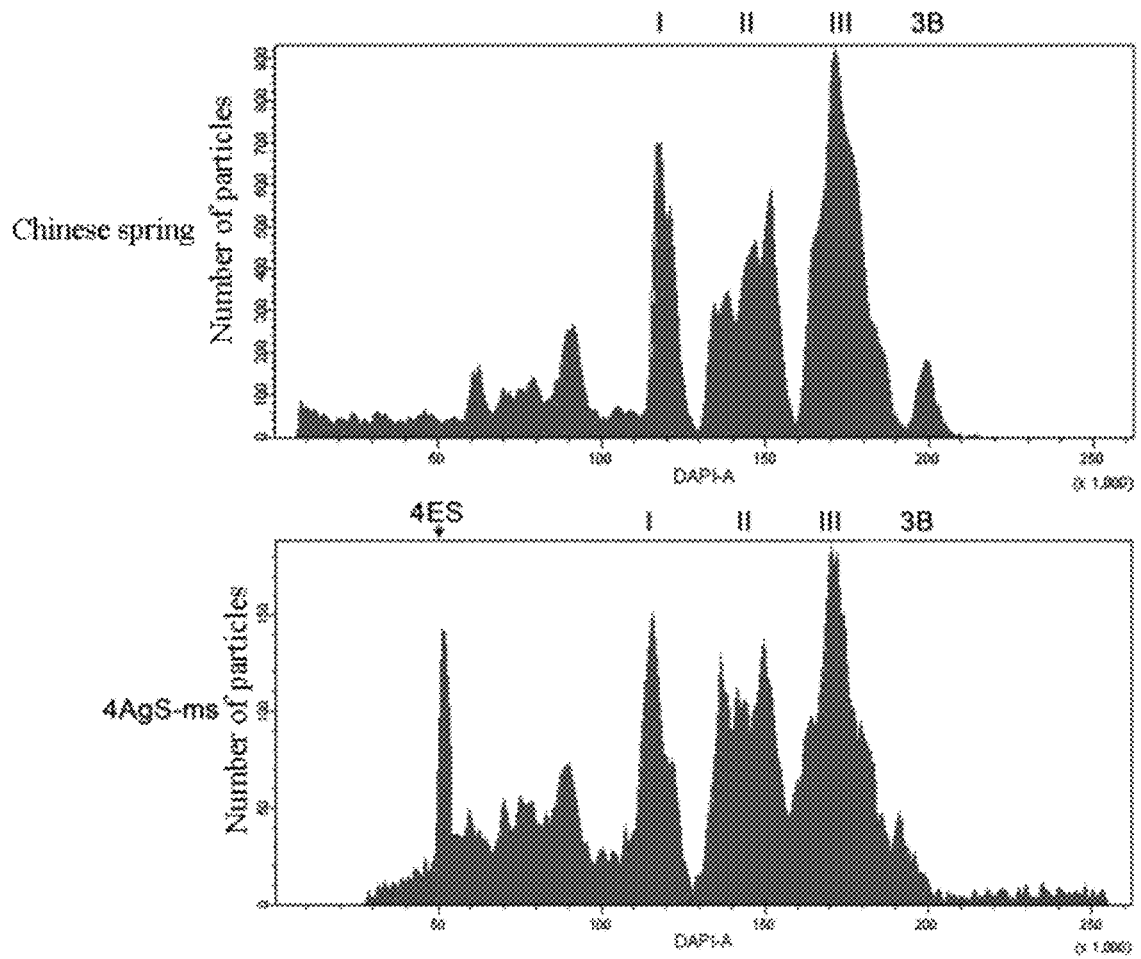
FIG. 2 graphically depicts the flow karyotype of Chinese spring and the 4AgS-ms alien ditelosomic addition line. The picture above was that of Chinese spring, and the picture below was that of the 4AgS-ms alien ditelosomic addition line. The horizontal ordinate was relative fluorescence intensity, and the vertical ordinate was a chromosome number. I, II, III, and 3B mark wheat chromosome groups in different sizes, and the peak labeled 4ES represents the telocentric chromosome 4AgS.

Because there is only one 4Ag chromosome in the 4Ag-ms alien monosomic addition line, blue grain (4Ag$^+$) and white grain (4Ag$^-$) segregation exists in its selfing seeds, wherein the plant of the blue grain is fertile, and the plant of the white grain is sterile. Through multi-generation selfing breeding of the 4Ag-ms alien monosomic addition line, a fertile plant line with white grains was obtained. GISH analysis (FIG. 1) showed that the 4Ag chromosome in this line was broken, most of the 4Ag chromosome was lost, and only a small part was remained in the wheat chromosomes. Therefore, the fertile plant line with white grains was named as a 4AgS-ms alien ditelosomic addition line.

After length measurement, it was estimated that the length of the 4AgS chromosome in the 4AgS-ms alien ditelosomic addition line was about ¼ of the longest wheat chromosome and about 250 Mb, remarkably shorter than that of all wheat chromosomes. The phenotype of 4AgS-ms alien ditelosomic addition line is white grain and fertile, indicating that the lost 4Ag chromosome comprises a blue grain gene Ba, and the remaining 4Ag comprises the fertility restoration gene1 (FRG1).

Embodiment 2. Separation of 4AgS Chromosome by Flow Cytometry

Cell cycle synchronization treatment was performed on a root tip cell of 4AgS-ms alien ditelosomic addition line by double-blocking method, followed by formaldehyde fixation, mechanical homogenization and DAPI staining, then chromosome analysis and sorting were done using flow cytometer.

Firstly, flow karyotype analysis was performed to confirm the size of the chromosome to be separated, with 4AgS-ms alien ditelosomic addition line as an experimental group and Chinese spring as a control group. Flow karyotype of Chinese spring comprised four independent peaks according to the sizes of chromosome; peak I comprised 4 chromosomes of 1D, 4D, 6D and 7D; peak II comprised 6 chromosomes of 1A, 3A, 6A, 2D, 3D and 5D; peak III comprised 10 chromosomes of 2A, 4A, 5A, 7A, 1B, 2B, 4B, 5B, 6B and 7B; peaked 3B represented chromosome 3B, which was the longest chromosome (Vrana et al., 2000). Compared with the karyotype of Chinese spring, there was another apparent small peak in the flow karyotype of 4AgS-ms alien ditelosomic addition line. According to the relative fluorescence intensity, the chromosome in this peak was estimated to be about 250 Mb in size, which was the target chromosome to be separated.

After multiple experiments, two million 4AgS chromosomes were isolated totally, the purity of which were identified as 88% by GISH analysis with the genomic DNA of *Thinopyrum ponticum* as a probe.

Embodiment 3. High-Throughput Sequencing and Sequence Assembly of 4AgS Chromosome The chromosomes separated by flow cytometry were highly-condensed chromatins, and cannot be directly applied to high-throughput sequencing. So, protease K digestion must be performed to release the DNA from the chromosomes. About 500 ng high quality of DNA were purified from 2.2 million 4AgS chromosomes.

Gene amplification was performed using Qiagen REPL1-g Single Cell Kit with 100 ng 4AgS genomic DNA as template, and 30 µg amplification products was obtained. Partial amplification products were digested and cloned into vector, and 31 clones were sequenced. In the 31 clones sequenced, there was no sequence from *E.coli* and the human genome, and only one sequence matching with wheat genome completely, and the rest sequences were likely from the 4AgS chromosome of *Thinopyrum ponticum*, which accounted for 97%.

Considering the high proportion of repetitive genome sequences (the proportion of repetitive sequence in wheat is about 80%) and the difficulty of chromosome assembly in Triticeae species, we adopted a strategy of combining second-generation and third-generation sequencing. The DNA was used to construct four sized sequencing libraries containing 300 bp, 500 bp, 2 Kb and 4 Kb fragment respectively. Second-generation sequencing of 125-bp paired-end was performed, and data of 20 Gb, 14 Gb, 6 Gb and 6 Gb, totaling 46 Gb, were obtained (equivalent to 184× 4AgS genomic coverage). A library of 10 Kb DNA insertion fragment was constructed and used in third-generation sequencing, and 5-10 Kb read lengths were acquired, which enhanced the de novo assembly of the chromosome sequence.

Firstly, the DNA reads of second-generation sequencing were assembled using *Platanus*, and a reference genome sequence of 212 Mb, with N50 length of 30 Kb, was obtained. Then, the DNA reads of third-generation sequencing were used for gap filling by sspace LR. Finally, a reference genome sequence of 234 Mb assembled in 17,302 scaffolds, with N50 length of 48 Kb, was obtained (Table 1).

TABLE 1

Assembly of 4AgS reference genome

| | Second-generation sequencing (bp) | Second-generation + third-generation sequencing (bp) |
|---|---|---|
| N90 | 548 | 8,437 |
| N80 | 1,720 | 16,753 |
| N70 | 8,525 | 25,781 |
| N60 | 20,468 | 36,063 |
| N50 | 30,872 | 48,049 |
| N40 | 42,508 | 61,983 |
| N30 | 55,064 | 79,946 |
| N20 | 73,456 | 104,370 |
| N10 | 109,141 | 155,763 |
| Max length | 252,461 | 411,726 |
| Mean | 1,412 | 13,581 |
| Median | 162 | 2582.5 |
| Min | 100 | 500 |
| Total base | 212,284,864 | 234,992,203 |
| Scaffold num | 150,241 | 17,302 |

Embodiment 4. Transcriptome Sequencing of 4AgS-Ms Alien Ditelosomic Addition Line RNA was extracted from microspore-stage anther of 4AgS-ms alien ditelosomic addition line and used for transcriptome sequencing, with Lanzhou genic male sterile mutant and corresponding parent as controls. 100-bp paired-end sequence reads were generated on an Illumina Hi-seq 2000, and 12 Gb valid data for each sample was obtained. Quality control was performed on the data, including removing the adapter sequences, excising the first 14 bp from 5'-end of reads, excising the bases with low quality value at both ends of reads, removing reads less than 50 bp and removing contaminated reads from human genome, *Escherichia coli* genome, wheat mitochondrial and chloroplast genome and ribosome rRNA of grass family. Finally, the clean reads were obtained.

Embodiment 5. Candidate Genes Obtained by Transcriptome and Collinearity Analysis The transcriptome data of 4AgS-ms alien ditelosomic addition line was aligned onto 17302 4AgS scaffolds without any mismatch (100% identity), and 2150 genes were obtained. Namely, 2150 genes on 4AgS chromosome are expressed in microspore-stage anther of 4AgS-ms alien ditelosomic addition line.

Because the purity of the 4AgS chromosome separated by flow cytometry was 88%, the assembled 4AgS scaffold contained a few of contaminated sequence from wheat genome. According to the principle that the fertility restoration gene1 (FRG1) to be searched is located on the 4AgS chromosome, and is expressed only in the 4AgS-ms alien ditelosomic addition line, but not in the controls of Lanzhou genic male sterile mutant and its parent, the genes also expressed in Lanzhou genic male sterile mutant and/or its parent were removed. Because the genes with higher expression level may be repetitive sequences, and the genes with lower expression level are less reliable, the genes, of which expression values are outside 10% and 90% of quantities, were also removed from the expression list of the 4AgS-ms alien ditelosomic addition line. Through the above two steps of screening, the candidate genes were reduced from 2150 to 374 (100% identity).

Figure 3:
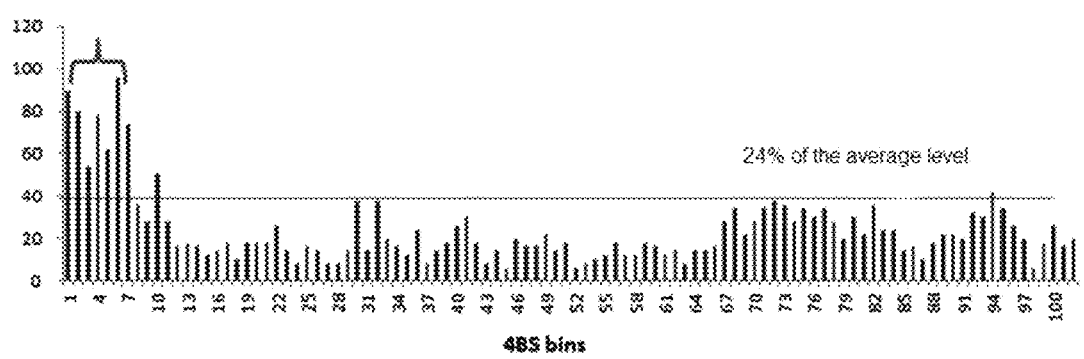
FIG. 3 graphically depicts the distribution of the percentages of genes in chr4B, the expression values of which in parent material were higher than that of Lanzhou genic male sterile mutant.

The transcriptome data of Lanzhou genic male sterile mutant and its parent was aligned to the IWGSC assembly with alignment tool tophat2, allowing at most two base mismatch. After the alignment, the number of reads from 2 samples in each locus was counted and converted to RPKM, respectively. Then, the difference of expression abundance of each gene represented by each locus in the 2 samples was calculated. If the FDR value was less than 0.001, it is considered that the difference of expression abundance of the gene in 2 samples was significant. The result showed that the difference between the parent and Lanzhou genic male sterile mutant was significant: Each half of the chromosome was divided to 100 parts, averagely. The percentage of genes was calculated, of which expression level in parents was significantly higher than that in Lanzhou genic male sterile mutant. It was discovered that almost all genes, within the distal 2-7% region of 4B short-arm, were expressed more highly in the parent material than in Lanzhou genic male sterile mutant. But the average percentage of genes, of which expression level in parents was significantly higher than that in Lanzhou genic male sterile mutant, was only 24% in the whole 4B chromosome. (FIG. 3). Thereby, we concluded that the Lanzhou genic male sterile mutant is caused by deletion of the distal 2-7% region of 4B short-arm.

Because there exists collinearity between 4AgS chromosome of *Thinopyrum ponticum* and 4BS chromosome of wheat, the full-length sequences (exon+intron) of the 374 genes were aligned to a TGAC-4BS reference genome of wheat using blastn with default parameters, and only 189 genes have homologous genes in 4BS chromosome. Among them, there were 8 genes located within the 2-7% region, and the 8 genes were the candidate genes of the fertility restoration gene (FRG1) of *Thinopyrum ponticum*.

Function annotation of the 8 candidate genes and their expressive abundance information in the 4AgS-ms alien ditelosomic addition line and the controls were shown in the following table 2.

TABLE 2

Gene expression and function annotation of candidate gene

| | Expressive abundance | | | |
|---|---|---|---|---|
| Gene ID | 4AgS-ms alien ditelosomic addition line | Parent | Lanzhou genic male sterile mutant | Function annotation |
| CUFF.1454 | 22 | 0 | 0 | Uncharacterized protein |
| CUFF.1544 | 338 | 0 | 0 | Inhibitor of Bruton tyrosine kinase |
| CUFF.1764 | 128 | 0 | 0 | Uncharacterized protein |
| CUFF.1962 | 29 | 0 | 0 | Uncharacterized protein |
| CUFF.199 | 17 | 0 | 0 | *Aspergillus niger* contig An11c0210 |
| CUFF.250 | 87 | 0 | 0 | Intracellular protein transport protein |
| CUFF.375 | 18 | 0 | 0 | Uncharacterized protein |
| CUFF.766 | 23 | 0 | 0 | Non-specific phospholipase C4 |

Embodiment 6. Transgenic Complementation

Genomic DNA sequences of the 8 candidate genes were inserted into the pAHC20 vector, respectively, and transformed into young embryo of 4Ag-ms alien monosomic addition line via particle bombardment. The pollen fertility of T0-generation transgenic plant without 4Ag chromosome (namely anzhou genic male sterile mutant background) was observed, which showed that only the vector containing the genomic DNA sequence of Gene ID CUFF.199 may complement the male sterile phenotype of the Lanzhou genic male sterile mutant, as showing in the following table 3. So, the corresponding gene of Gene ID CUFF.199 was Fertility restoration gene1 (FRG1) in *Thinopyrum ponticum*. Its genomic DNA sequence is shown in SEQ ID NO:1, CDS sequence is shown in SEQ ID NO:2, protein sequence is shown in SEQ ID NO:3, promoter sequence is shown in SEQ ID NO: 4, and terminator sequence is shown in SEQ ID NO: 5.

TABLE 3

Pollen fertility of transgenic T0-generation plants with candidate gene

| Candidate gene ID | Plant number of homozygous LZ mutation background | Plant number of pollen fertile | Plant number of pollen sterile |
|---|---|---|---|
| CUFF.1454 | 10 | 0 | 10 |
| CUFF.1544 | 7 | 0 | 7 |
| CUFF.1764 | 12 | 0 | 12 |
| CUFF.1962 | 6 | 0 | 6 |
| CUFF.199 | 9 | 9 | 0 |
| CUFF.250 | 10 | 0 | 10 |
| CUFF.375 | 8 | 0 | 8 |
| CUFF.766 | 9 | 0 | 9 |

Embodiment 7. Construction and Function Analysis of FRG1 Gene Promoter Expression Vector The genomic DNA of 4AgS-ms alien ditelosomic addition line was used as template to amplify the 2265 bp promoter of FRG1 gene. The promoter sequence was shown in SEQ ID NO: 4. The amplification product was inserted into pAHC20-GUS vector through an In-fusion method, and the expression vector pAHC20-pFRG1-GUS was obtained.

Then, pAHC20-pFRG1-GUS plasmid was transformed into wheat young embryo via particle bombardment, and 16 transgenic plants were obtained. GUS staining of roots, stems, leaves and flowers at different development stages of the transgenic plants showed that the promoter of FRG1 gene may drive GUS to be specifically expressed in wheat pollen, which indicating that the promoter of FRG1 gene is a pollen-specific promoter.

Embodiment 8. Application of FRG1 Gene in New Generation Wheat Hybrid Breeding Technology FRG1 gene could be applied in a new generation hybrid breeding technology, and the core idea of the technology was as follows: a wheat recessive genic male sterile mutant is used as a transformation acceptor material, and three closely-linked target genes are transformed to the sterile mutant, wherein the fertility restoration gene can restore the fertility of the sterile transformation acceptor; a pollen inactivation gene can inactivate the pollen grains containing exogenous genes, namely, the fertilization ability of those pollen grains is lost; a seed-marker gene can be used for sorting the transgenic seeds and the non-transgenic seeds, the sorted non-transgenic seeds can be used as the sterile line, and the transgenic seeds can be used as the maintenance line. Or, the maintenance line could pollinate the sterile line, so that the sterile line is propagated, while the maintenance line can self-pollinate to produce the offspring as the new generation of maintainer line. Because the technology utilizes biotechnology to produce a non-transgenic product, the bottleneck problem in the wheat hybrid seed production: low resource utilization in three-line hybrid breeding system and the instability of the sterile line in two-line hybrid breeding system, can be solved.

The above hybrid breeding technology of the invention is suitable for the propagation and maintenance of a Lanzhou genic male sterile mutant and a allelic mutant thereof. According to the above theory, firstly, the three expression cassettes, ZmBT1-ZmAA, FRG1 and mCherryW were transformed into the wheat by the inventors respectively, and functions of each expression cassette were further verified. The result showed that each expression cassette worked well when they were transformed into the wheat independently. The expected effect of the design was achieved.

Further, the inventors constructed a pAHC20-FRG1-AA-mCherryW vector through assembling the following DNA elements:

1) The pAHC20 vector was used as the backbone;
2) FRG1 gene expression cassette included target gene FRG1, promoter and terminator thereof, which are all from *Thinopyrum ponticum*. The promoter sequence of the FRG1 gene is shown in SEQ ID NO: 4, the terminator sequence of the FRG1 gene is shown in SEQ ID NO: 5, the genome DNA sequence of the FRG1 gene is shown in SEQ ID NO: 1, and the protein amino acid sequence encoded by the nucleotide sequence of the FRG1 gene is shown in SEQ ID NO: 3;
3) Gene expression cassette PG47: ZmBT1-ZmAA-IN2-1: the open reading frame ZmBT1-ZmAA (nucleotide sequence is shown in SEQ ID NO: g composed of target gene ZmAA and transit peptide ZmBT1 was connected to the downstream of promoter PG47 (nucleotide sequence is shown in SEQ ID NO: 7) and the upstream of terminator 1N2-1 (nucleotide sequence is shown in SEQ ID NO: 8);
4) Gene expression cassette CaMV35S enhancer-LTP2: mCherryW-PINII: the open reading frame of mCherryW gene (SEQ ID NO: 9) was connected between the CaMV355 enhancer-LTP2 promoter (SEQ ID NO: 10) and the PINII terminator (SEQ ID NO: 11) to produce the gene expression cassette of mCherryW (CaMV35S enhancer-LTP2: mCherryW-PINII).

Wheat transformation: The plasmid pAHC20-FRG1-AA-mCherryW was transformed into young embryo of 4Ag-ms alien monosomic addition line via particle bombardment. Through processes of selection, regeneration, rooting, molecular identification by PCR, etc., the single-copy transgenic plants, without 4Ag chromosome of *Thinopyrum ponticum* in homozygous Lanzhou genic male sterile mutant background, were obtained.

Pollen fertility detection of transgenic wheat plant: The pollen activity detection was performed on the above plants. The method specifically includes the following steps: one flower was taken from each of the transgenic plants and non-transgenic plants; 1 anther was taken from each flower, and placed at the center of a glass slide; a drop of 1% of $I_2$-KI solution was added; pollen grains were released with tweezers and a dissecting needle, then covered by a cover glass and observed under a microscope; and the number of sterile pollen grains and total number of the pollen grains were counted (the pollen grains with dark-blue by $I_2$-KI staining were the fertile, and the pollen grains which cannot be stained by $I_2$-KI solution were sterile). The result showed that, the proportion of the sterile pollen grains to total pollen grains in the non-transgenic plant was less than 2%, and the proportion of the sterile pollen grains to total pollen grains in many transgenic plants were about 50%. It is indicated that the vector provided by the invention can achieve the expected function of inactivating pollen.

Segregation analysis of fluorescence seeds and non-fluorescence seeds in the offspring of transgenic wheat plant: The segregation proportion survey of fluorescence seeds and non-fluorescence seeds was performed on T1-generation seeds generated by the transgenic plant, and showed 1:1 segregation ratio, indicating that the elements of the vector provided by the invention were well expressed as a whole, and the purpose of creating and breeding sterile line can be realized; wherein a FRG1 gene can restore the fertility of the male sterile mutant acceptor, the expression of ZmBT1-ZmAA gene and mCherryW gene can achieve the expected function of inactivating pollen and markering seeds by fluorescence, respectively.

What is claimed is:

1. An expression vector, the expression vector comprises an recombinant expression cassette which comprises a fertility restoration gene, wherein the fertility restoration gene comprises a heterologous nucleic acid molecule comprising a nucleotide sequence selected from the group consisting of (a) the nucleotide sequence as shown in SEQ ID NO: 1 encoding the amino acid sequence of SEQ ID NO: 3; (b) the nucleotide sequence as shown in SEQ ID NO: 2 encoding the amino acid sequence of SEQ ID NO: 3; and (c) a nucleotide sequence encoding the amino acid sequence as shown in SEQ ID NO: 3.

2. The expression vector as claimed in claim 1, wherein the fertility restoration gene is operably connected with a promoter driving expression thereof, and the promoter, is selected from the group consisting of a constitutive expression promoter, a inducible promoter, a tissue-specific promoter and a spatiotemporal-specific promoter.

3. The expression vector as claimed in claim 2, wherein the tissue-specific promoter is a pollen-specific promoter.

4. The expression vector as claimed in claim 1, wherein the expression vector further comprises a pollen inactivation gene, and wherein the pollen inactivation gene disturbs the function or formation of a male gamete comprising the pollen inactivation gene.

5. The expression vector as claimed in claim 4, wherein the pollen inactivation gene comprises a barnase gene, an amylase gene or a DAM methylase gene.

6. The expression vector as clamed in claim 1, wherein the expression vector further comprises a selection gene, and wherein the selection gene is used for selecting a plant, a plant tissue cell or a vector comprising the expression vector.

7. The expression vector as claimed in claim 6, wherein the selection gene comprises an antibiotic-resistance gene, herbicide-resistance gene or a fluorescent protein gene.

8. A method for restoring male plant fertility, comprising transforming a Lanzhou genic male sterile mutant plant with the expression vector of claim 1, wherein transgenic expression of the protein as shown in SEQ ID NO: 3 restores the male fertility of the Lanzhou genic male sterile mutant plant transformed with said expression vector.

9. The method as claimed in claim 8, wherein the fertility restoration gene is operably connected with a pollen-specific promoter for driving the fertility restoration gene expression in pollen tissue of said transformed Lanzhou genic male sterile mutant plant.

10. The method as claimed in claim 9, wherein the pollen-specific promoter is the promoter of a fertility regulation gene, wherein the fertility regulation gene is selected from the group consisting of MS26, NP1, MSP1, PAIR1, PAIR2, ZEP1, MELL, PSS1, TDR, UDT1, GAMYB4, PTC1, API5, WDA1, CYP704B2, MS22, DPW, MADS3, OSC6, RIP1, CSA, AID1, 5126, Ms45 and FRG1.

11. The method as claimed in claim 10, wherein the pollen-specific promoter has the nucleotide sequence as shown in SEQ ID NO: 4.

12. The expression vector as claimed in claim 3, wherein the pollen-specific promoter has the nucleotide sequence as shown in SEQ ID NO: 4.

13. The expression vector as claimed in claim 5, wherein the pollen inactivation gene is a corn α-amylase gene.

14. The expression vector as claimed in claim 5, wherein the pollen inactivation gene has the nucleotide sequence as shown in SEQ ID NO: 6.

15. The expression vector as claimed in claim 7, wherein the selection gene comprises a chloramphenicol-resistance gene, a hygromycin-resistance gene, a streptomycin-resistance gene, a miramycin-resistance gene, a sulfonamide-resistance gene, a glyphosate-resistance gene, a phosphinothricin-resistance gene, a bar gene, a red fluorescence gene DsRED, a mCherry gene, a cyan fluorescence protein gene, a yellow fluorescence protein gene, a luciferase gene or a green fluorescence protein gene.

* * * * *